United States Patent [19]
Brodie et al.

[11] 4,329,453
[45] May 11, 1982

[54] CEPHALOSPORIN ANTIBIOTIC

[75] Inventors: Alastair C. Brodie, Ickenham; Lewis A. Wetherill, North Wembley, both of England

[73] Assignee: Glaxo Group Limited, London, England

[21] Appl. No.: 185,883

[22] Filed: Sep. 9, 1980

[30] Foreign Application Priority Data

Oct. 2, 1979 [GB] United Kingdom ............... 34204/79

[51] Int. Cl.$^3$ ........................................... C07D 501/46
[52] U.S. Cl. ........................................ 544/25; 424/246
[58] Field of Search ........................... 424/246; 544/25

[56] References Cited
U.S. PATENT DOCUMENTS
4,258,041 3/1981 O'Callaghan et al. ............... 544/25

*Primary Examiner*—Paul M. Coughlan, Jr.
*Attorney, Agent, or Firm*—Bacon & Thomas

[57] ABSTRACT (6R,7R)-7-[(Z)-2-(2-Aminothiazol-4-yl)-2-(2-carboxyprop-2-oxyimino)acetamido]-3-(1-pyridiniummethyl)-ceph-3-em-4-carboxylate in the form of its crystalline pentahydrate. This pentahydrate has a well defined crystalline structure and exhibits good stability on storage. The pentahydrate exhibits excellent antibiotic activity, particularly against organisms which are normally difficult to combat with β-lactam antibiotics.

1 Claim, 1 Drawing Figure

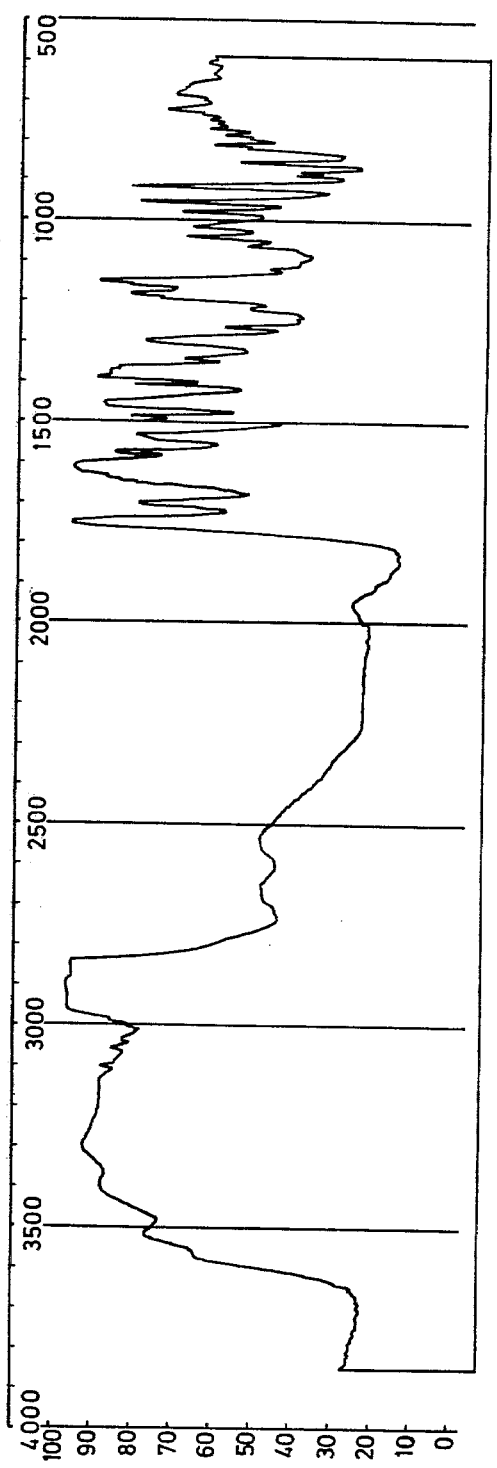

CEPHALOSPORIN ANTIBIOTIC

This invention relates to improvements in or relating to (6R,7R)-7-[(Z)-2-(2-aminothiazol-4-yl)-2-(2-carboxy-prop-2-oxyimino)acetamido]-3-(1-pyridiniummethyl)-ceph-3-em-4-carboxylate of formula

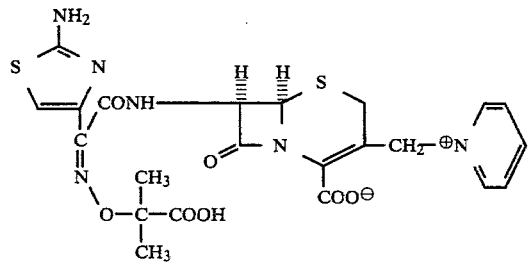
(I)

This compound, which is variously referred to as 'ceftazidime' and 'GR 20263', has been found to have broad spectrum antibiotic activity and, in particular, unusually high activity against gram-negative organisms, including many β-lactamase-producing gram-negative strains, as described in our U.K. Patent Specification No. 2025398. The compound possesses excellent activity against organisms normally difficult to combat with β-lactam antibiotics, such as indole-positive Proteus, Serratia, Providence and especially Pseudomonas organisms, and its antibacterial properties are not impaired by human serum. Moreover, the effect of increased inocula against the compound is low and the compound is rapidly bactericidal at concentrations close to the minimum inhibitory concentration. It is well distributed in the bodies of small rodents giving useful therapeutic levels after subcutaneous injection. Experimental infections in mice with gram-negative bacteria have been successfully treated using the compound and, in particular, excellent protection has been obtained against strains of Pseudomonas aeruginosa, an organism normally not susceptible to treatment with cephalosporin antibiotics. This protection was comparable with the treatment with an aminoglycoside such as amikacin. Acute toxicity tests with the compound in mice gave $LD_{50}$ values in excess of 6 g/kg. No nephrotoxicity has been observed in rats at dosages of 2.0 g/kg. In studies in human volunteers the compound has shown good pharmacokinetic properties, giving high and long lasting serum levels after injection. The long serum half-life suggests that less frequent dosages might be required for less serious infections. Early clinical results suggest that the compound reproduces in the clinic the excellent antibiotic properties demonstrated in vitro and in experimental animals.

U.K. Patent Specification No. 2025398 also discloses solvates and non-toxic salts, e.g. base salts and acid addition salts, of the above-mentioned cephalosporin compound.

U.K. Patent Specification No. 2025398 discloses, inter alia, a method for the preparation of the above-mentioned cephalosporin compound (I) as well as solvates and non-toxic salts thereof, which comprises:
acylating a compound of formula

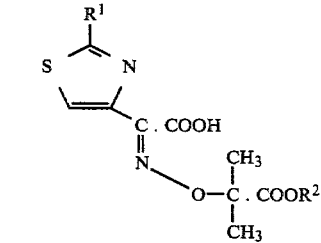

preferably as the bishydrochloride acid addition salt, with an acid of formula $$
\begin{array}{c}
R^1 \\
S \diagup N \\
\diagdown C . COOH \\
N \\
\diagdown O-C . COOR^2 \\
CH_3
\end{array}
$$

(wherein $R^1$ represents an amino or protected amino group; and $R^2$ represents a carboxyl blocking group) or with an acylating agent corresponding thereto; whereafter the following reactions may be carried out
 (i) removal of any amino-protecting group and the carboxyl blocking group $R^2$, and, if desired,
 (ii) conversion of a carboxyl group into a non-toxic salt.

The desired compound of formula (I) above of U.K. Patent Specification No. 2025398 was obtained as an amorphous solid and its stability was not particularly satisfactory, especially at elevated temperatures.

It has not been found that (6R,7R)-7-[(Z)-2-(2-aminothiazol-4-yl)-2-(2-carboxyprop-2-oxyimino)acetamido]-3-(1-pyridiniummethyl)ceph-3-em-4-carboxylate (I) can be advantageously prepared and isolated in the form of a crystalline hydrate, which by analysis is a pentahydrate, which pentahydrate forms one aspect of the invention.

The new hydrate of the cephalosporin compound (I) is of superior quality in terms of its crystallinity and stability, as well as being of increased purity. In particular, the new hydrate has been found to have a well-defined crystalline structure and it has been found to be remarkably stable even when stored at a temperature of 50° C. for an extended period. These properties render the hydrate of value in pharmaceutical use.

It has been found that the new crystalline hydrate can be conveniently prepared from a solution of a salt of the above cephalosporin compound. Thus, in another aspect the invention provides a process for the preparation of (6R,7R)-7-[(Z)-2-(2-aminothiazol-4yl)-2-(2-carboxyprop-2-oxyimino)acetamido]-3-(1-pyridiniummethyl)ceph-3-em-4-carboxylate pentahydrate which comprises adjusting the pH of a solution of an acid or base salt of (6R,7R)-7-[(Z)-2-(2-aminothiazol-4-yl)-2-(2carboxyprop-2-oxyimino)acetamido]-3-(1-pyridiniummethyl)ceph-3-em-4-carboxylate in an aqueous medium to 3.3 to 4, e.g. about 3.7, and crystallising the desired pentahydrate. For example, it has been found that the desired crystalline hydrate may be precipitated from an aqueous solution of acid addition salt on addition of an organic or inorganic base to a pH in the range 3.3 to 4.0.

Bases which may be used in the precipitation include, for example, inorganic bases such as alkali or alkaline earth metal hydroxides, carbonates or bicarbonates e.g. sodium carbonate, sodium bicarbonate and sodium hydroxide. A starting acid addition salt may be formed with an organic or inorganic acid. Examples of organic acids which may be used include carboxylic and sulphonic acids such as formic, trifluoroacetic, toluene-p-sulphonic or methanesulphonic acids. Examples of inorganic acids which may be used include mineral acids such as hydrochloric, hydrobromic, sulphuric, nitric or phosphoric acid. A particularly suitable acid addition salt is the bishydrochloride of compound (I), which may be obtained in highly pure form.

Alternatively the new pentahydrate may be prepared by addition of an acid to a solution of a base salt of compound (I) in an aqueous medium to a pH in the range 3.3 to 4.0. Acids which may be used for this purpose include organic and inorganic acids such as, for example, hydrochloric acid and sulphuric acid. Starting base salts include, for example, alkali metal salts, e.g. sodium and potassium salts; alkaline earth metal salts e.g. a calcium salt; amino acid salts e.g. lysine and arginine salts; and organic base salts e.g. procaine, phenethylbenzylamine, dibenzylethylenediamine, ethanolamine, diethanolamine and N-methyl-glucosamine salts.

If desired, the aqueous medium may contain a water-miscible organic solvent such as acetone.

The precipitation is preferably effected at a temperature of from 0° to 50° C., e.g. 15° to 40° C., conveniently at about 24° C., followed where necessary by a step of cooling to enhance crystal yield to a temperature in the range from 0° to 10° C.

After precipitation, the pentahydrate product may be recovered by filtration and washed and dried in conventional manner. For example the hydrate may conveniently be dried by air drying, careful drying under reduced pressure or, preferably, in a sterile inert gas atmosphere such as sterile nitrogen.

The salts for use in the preparation of the new pentahydrate according to the invention may be prepared by a process disclosed in the above-mentioned U.K. Patent Specification No. 2025398, i.e. by a process corresponding to the method above mentioned. The hydrochloride may be prepared in the form of a highly stable crystalline bishydrochloride product by crystallisation from a medium comprising acetone and formic acid e.g. under the conditions described in the Preparation 1 below.

The new crystalline pentahydrate according to the invention has been subjected to X-ray powder diffraction studies. The product of the following Example 2 was used to obtain a Debye Scherrer powder diffraction photograph by exposure for 12 hours to CoKα radiation and a second photograph by exposure for 3 hours to CuKα radiation. The line intensities were compared against a set of standards to give the relative intensities shown in the following Table:

TABLE

| 'd' value (Å) | Intensity* | 'd' value (Å) | Intensity* |
|---|---|---|---|
| 15.9 | m | 3.24 | 2vw |
| 9.9 | s | 3.18 | w |
| 8.7 | s | 3.13 | w |
| 7.9 | tr | 3.01 | m |
| 6.7 | md | 2.87 | m |
| 6.3 | w | 2.77 | m |
| 5.95 | m | 2.72 | w |
| 5.74 | w | 2.69 | wd |
| 5.42 | w | 2.52 | m |
| 5.18 | m | 2.43 | w |
| 4.71 | m | 2.33 | w |
| 4.50 | m | 2.29 | vw |
| 4.37 | tr | 2.26 | vw |
| 4.15 | tr | 2.23 | vw |
| 4.10 | s | 2.19 | w |
| 4.01 | m | 2.13 | vw |
| 3.93 | w | 2.07 | w |
| 3.86 | s | 2.03 | w |
| 3.68 | s | 1.97 | vw |
| 3.41 | w | 1.94 | vw |
| 3.33 | 2vw | | |
| 3.29 | 2vw | | |

*s = strong, m = medium, w = weak, v = very, 2v = vv, d = diffuse, tr = trace

The new pentahydrate according to the invention has also been characterised by its infrared spectrum. The infrared spectrum of the product of the following Example 2 in Nujol was obtained and this is shown in the FIGURE of the accompanying drawing.

The following Examples serve to illustrate the preparation of the pentahydrate according to the invention. Preparation 1 illustrates the preparation of an acid addition salt starting material for the preparation of the pentahydrate. In the Preparation and Examples all temperatures are in °C., and TFA is trifluoroacetic acid.

Proton magnetic resonance (p.m.r.) spectra were determined at 100 MHz. The integrals are in agreement with the assignments, coupling constants, J, are in Hz, the signs not being determined: S=singlet, t=triplet, d=doublet, dd=double doublet, m=multiplet and ABq=Ab quartet. Amberlite L.A.2 is a weakly basic high molecular weight secondary amine sold by Rohm and Haas, Philadelphia, USA. Hyflo Super-Cel is a diatomaceous silica filter aid sold by Johns-Manville, U.S.A.

Preparation 1

(6R,7R)-7-[(Z)-2-(2-Aminothizol-4-yl)-2-(2-carboxy-prop-2-oxyimino)acetamido]-3-(1-pyridiniummethyl)-ceph-3-em-4-carboxylate bishydrochloride Formic acid (84 ml) was added with stirring to (6R,7R)-7-[(Z)-2-(2-tritylaminothiazol-4-yl)-2-(2-t-butoxycarbonylprop-2-oxyimino)acetamido]-3-(1-pyridiniummethyl)ceph-3-em-4-carboxylate, N,N-dimethylformamide solvate (41.8 g), water cooling being employed to maintain the temperature below 28°. The resulting solution was cooled to 20°, and concentrated hydrochloric acid (17.0 ml) added with stirring over 5 minutes. The mixture was stirred for 3 hours at room temperature, then filtered to remove triphenylmethanol. The filtrate was added to stirred acetone (800 ml). The triphenylmethanol was washed with formic acid (3×7 ml), and the combined washings were added to the filtrate-acetone mixture. The resulting suspension was stirred for 1.25 hours, then filtered. The crystalline solid was washed with acetone and dried in vacuo to give the title compond (20.2 g), Chlorine, found: 11.0%; calculated for $C_{22}H_{24}N_6O_7S_2Cl_2$:11.5%; $\lambda_{max}$ (pH 6 phosphate buffer) 257 nm ($E_{1\,cm}^{1\%}$ 347), $\lambda_{inf}$ at 240 ($E_{1\,cm}^{1\%}$ 310) and 290 nm ($E_{1\,cm}^{1\%}$ 150).

All the following Examples illustrate the preparation of (6R, 7R)-7-[(Z)-2-(2-aminothiazol-4-yl)-2-(2-carboxyprop-2-oxyimino)acetamido]-3-(1-pyridinium-methyl)-ceph-3-em-4-carboxylate pentahydrate.

EXAMPLE 1

The bishydrochloride (2.56 g), prepared as in Preparation 1, dissolved in distilled water (8 ml) was stirred for 2 to 3 minutes until clear, whereafter 98% formic acid (1.0 ml) was added. This mixture was stirred with a liquid anion exchange resin, 'Amberlite' L.A.2, (4 ml) in diisopropyl ether (8 ml), allowed to settle and separated. The aqueous layer was extracted with diisopropyl ether (2×5 ml) and the resin layer was back-washed with distilled water (5 ml), which in turn was extracted with the two diisopropyl ether extracts. The combined aqueous layers (pH ca. 2.4), which contained the formate salt, were stirred during the addition of ammonia solution (8 to 10 drops) to pH 3.7 and the clear solution allowed to crystallise slowly at ambient temperature for one hour and then at 0° overnight.

The title compound was collected by filtration, washed with chilled distilled water (2×6 ml), and with acetone (2×10 ml) and dried at ambient temperature in an air oven for 2 hours to yield a crystalline solid (2.0 g), $\lambda_{max}$ (pH 6 buffer) 257 nm ($E_1\ _{cm}^{1\%}$ 348); $\tau(D_O+TFA)$ 0.98, 1.36 and 1.84 (pyridinium protons), 2.80 (-thiazole), 4.05 ($C_7$—H), 4.15 and 4.58 (—$CH_2$—), 4.64 ($C_6$—H), 6.21 and 6.67 ($C_2$—H) and 8.40 (—$(CH_3)_2$); $\nu_{max}$ (Nujol) 1760 ($\beta$-lactam), 1710 ($CO_2H$), 1645 and 1538 (CONH) and 1620 cm$^{-1}$ ($CO_2^-$); water (Karl Fischer) 13.6%; residual chlorine, <0.1%, $C_{22}H_{22}N_6O_7S_2.5H_2O$ requires water, 14.1%.

EXAMPLE 2

The bishydrochloride, prepared as in Preparation 1, (2.0 g) was dissolved in distilled water (12 ml) and stirred during the addition of ammonia solution to pH 3.5. The clear solution was allowed to crystallise at ambient temperature for 0.5 hour; the pH was adjusted to 3.8 with ammonia solution and the suspension was then kept at 0° for 1 hour.

The title compound was collected by filtration, washed with chilled water (10 ml) and with acetone and dried at ambient temperature in vacuo for 3 hours to yield 1.54 g of crystalline solid; $\lambda_{max}$ (pH 6 buffer) 257 nm ($E_1\ _{cm}^{1\%}$ 356); $\tau(D_2O+TFA)$, resembles Example 1 above; $\nu_{max}$ (Nujol) see FIGURE; water (Karl Fischer method) 13.8%; residual chlorine <0.1%; found C, 41.5; H, 4.73; N, 13.17%, $C_{22}H_{22}N_6O_7S_2$, $5H_2O$ requires C, 41.5; H, 5.05; N, 13.2; $H_2O$, 14.1%. A Debye Scherrer X-ray powder diffraction photograph was obtained on the product; the results are given above.

EXAMPLE 3

The bishydrochloride prepared as in Preparation 1 (2.0 g) was dissolved in distilled water (6 ml) and stirred during the slow addition of 2 N-sodium hydroxide solution to a pH of 3.8. When crystallisation was well established, the pH which had risen to 4.5, was brought back to 3.8 with 2 N-hydrochloric acid (a few drops). The suspension was cooled in ice and the title compound was collected by filtration, washed with ice water (10 ml) and with acetone and dried at room temperature in air oven for 2 hours to yield 1.56 g of crystalline solid; $\lambda_{max}$ (pH 6 buffer) 257 nm ($E_1\ _{cm}^{1\%}$ 354); $\tau(D_2O+TFA)$ resembles Example 1 above; water (Karl Fischer) 14.4%; residual chlorine, <0.1%.

EXAMPLE 4

The bishydrochloride prepared as in Preparation 1 (4.0 g) was dissolved in distilled water (14 ml) and stirred during the addition of saturated aqueous sodium bicarbonate solution (13 ml) to pH 3.8. The product crystallised rapidly and the suspension was cooled in ice. The title compound was collected by filtration, washed with ice-cold water (20 ml) and with acetone and dried at room temperature in an air oven for 2 hours to yield 3.1 g of crystalline solid $\lambda_{max}$ (pH 6 buffer) 257 nm ($E_{1cm}^{1\%}$ 358), 241 nm ($E_1\ _{cm}^{1\%}$ 322), 290 nm ($E_1\ _{cm}^{1\%}$ 157). Water (Karl Fischer) 13.9%, $\nu_{max}$ (Nujol) resembles Example 1 above.

EXAMPLE 5

The material prepared as in Example 3 (200 g) was suspended in water (720 ml) at 20° and treated with 2 N-sodium hydroxide until solution was complete at pH 6. The solution of the sodium salt thus produced now at 22°, was stirred with 'Hyflo Super-Cel' (2 g) and filtered through a No. 5 porosity sintered glass filter followed by a water wash (80 ml). The clarified solution was adjusted to pH 3.75 with 2 N-sulphuric acid and seeded at 23°. After 30 minutes standing, the suspension was readjusted to pH 3.75 (from 4.2) and slowly stirred whilst cooling to 12° and the pH again adjusted to 3.75. The product was collected by filtration, washed with ice-cold water (800 ml) and with acetone (800 ml) and dried in an air oven at 21° overnight to yield sterile title compound (165.6 g). Water (Karl Fischer) 1.4.2%, $\tau$ resembles that of Example 1.

PHARMACEUTICAL FORMULATIONS

The crystalline pentahydrate of the present invention exhibits the antibiotic properties of the above-mentioned compound (I) and may be used for treating a variety of diseases caused by pathogenic bacteria in human beings and animals, such as respiratory tract infections and urinary tract infections.

In another aspect, the present invention provides pharmaceutical compositions containing the new pentahydrate adapted for use in human or veterinary medicine. Such compositions may be presented in conventional manner with the aid of any necessary pharmaceutical carriers or excipients.

The antibiotic pentahydrate compound according to the invention may be formulated for injection and may be presented in unit dose form in ampoules, or in multi-dose containers if necessary with an added preservative.

The compositions may also take such forms as suspensions, solutions or emulsions in oily or aqueous vehicles, and may contain formulatory agents such as suspending, stabilising and/or dispersing agents. Desirably the active ingredient may be in powder form for constitution with a suitable vehicle, e.g. sterile, pyrogen-free water, before use. Preferably such powder formulations may contain an appropriate non-toxic base in order to improve the water-solubility of the active ingredient and/or to ensure that when the powder is constituted with water, the pH of the resulting aqueous formulation is physiologically acceptable. Alternatively, the base may be present in the water with which the powder is constituted. The base may be, for example, an inorganic base such as sodium carbonate, sodium bicarbonate, trisodium orthophosphate or sodium sulphite or an organic base such as lysine, lysine acetate, tromethamine, arginine or sodium glycinate.

The antibiotic compound may also be formulated as suppositories e.g. containing conventional suppository bases such as cocoa butter or other glycerides.

For medication of the eyes or ears, the preparations may be formulated as individual capsules, in liquid or semi-liquid form, or as drops.

Compositions for veterinary medicine may also, for example, be formulated as intramammary preparations in either long acting or quick-release bases.

The compositions may contain from 0.1% upwards, e.g. 0.1–99%, of the active material, depending on the method of administration. When the compositions comprise dosage units, each unit will preferably contain 50–1500 mg of the active ingredient. The dosage as employed for adult human treatment will preferably range from 500 to 6000 mg per day, depending on the route and frequency of administration. For example, in adult human treatment 1000 to 3000 mg per day administered intravenously or intramuscularly should normally suffice. In treating Pseudomonas infections higher daily doses may be required.

The antibiotic compound according to the invention may be administered in combination with other therapeutic agents such as antibiotics, for example penicillins or other cephalosporins.

The following Formulations illustrate the pharmaceutical compositions:

FORMULATION A, for injection

Formula per vial (6R,7R)-7-[(Z)-2-(2-Aminothiazol-4-yl)-2-(2-carboxyprop-2-oxyimino)acetamido]-3-(1-pyridiniummethyl)ceph-3-em-4-carboxylate pentahydrate: 582 mg
Sodium carbonate (anhydrous): 58 mg

Method

The cephalosporin hydrate was blended with sodium carbonate and filled into a glass vial. The vial headspace was purged with nitrogen and a combination seal applied by crimping. The product was dissolved, as for administration, by addition of 2 ml Water for Injections.

FORMULATION B, Injection twin-pack (a) Fill sterile (6R,7R)-7-[(Z)-2-(2-aminothiazol-4-yl)-2-(2-carboxyprop-2-oxyimino)acetamido]-3-(1-pyridiniummethyl)ceph-3-em-4-carboxylate pentahydrate aseptically into glass vials under a blanket of sterile nitrogen, such that each vial contains an amount equivalent to 500 mg of the anhydrous cephalosporin. Close the vials using rubber disks or plugs, held in position by aluminium overseals, thereby preventing gaseous exchange or ingress of microorganisms.

(b) Prepare a 3.84% w/v solution of sodium bicarbonate, clarify by filtration and fill 2.15 ml into clean ampoules. Pass carbon dioxide into the contents of each ampoule for one minute before sealing. Sterilise the ampoules by autoclaving and check for clarity.

(c) Constitute the cephalosporin antibiotic shortly before administration by dissolving in 2.0 ml of the sodium bicarbonate solution.

FORMULATION C, for injection

Formula per vial (6R,7R)-7-[(Z)-2-(2-Aminothiazol-;b 4-yl)-2-(2-carboxyprop-2-oxyimino)acetamido]-3-(1-pyridiniummethyl)ceph-3-em-4-carboxylate pentahydrate: 582 mg
L-Arginine: 167 mg

Method

The cephalosporin was blended with L-arginine and filled into a glass vial. The vial headspace was purged with nitrogen and a combination seal applied by crimping. The product was dissolved as for administration, by the addition of 1.5 ml Water for Injection.

FORMULATION D, for injection

Formula per vial (6R,7R)-7-[(Z)-2-(2-Aminothiazol-4-yl)-2-(2-carboxyprop-2-oxyimino)acetamido]-3-(1-pyridiniummethyl)ceph-3-em-4-carboxylate pentahydrate: 582 mg
L-Arginine: 167 mg
Sodium dihydrogen phosphate dihydrate: 15 mg

Method

Mix the sterile L-arginine and sterile sodium dihydrogen phosphate under aseptic conditions. Blend aseptically the resultant powder mix with the sterile cephalosporin. Fill aseptically into glass vials under a blanket of sterile nitrogen. Close the vials using rubber discs, or plugs, held in position by aluminium overseals, thereby preventing gaseous exchange or ingress of microorganisms. Reconstitute the product by dissolving in Water for Injections or other suitable sterile vehicle shortly before administration.

We claim:

1. (6R,7R)-7-[(Z)-2-(2-Aminothiazol-4-yl)-2-(2-carboxyprop-2-oxyimino)acetamido]-3-(1-pyridiniummethyl)ceph-3-em-4-carboxylate pentahydrate.

* * * * *